US007579027B2

(12) United States Patent
Birketvedt

(10) Patent No.: US 7,579,027 B2
(45) Date of Patent: Aug. 25, 2009

(54) COMPOSITION FOR TREATING OBESITY COMPRISING EXTRACT FROM WHITE KIDNEY BEANS, RED KIDNEY BEANS, AND GREEN TEA LEAVES

(76) Inventor: Grethe Stoa Birketvedt, c/o Thomas L. Rich, 446 E. 20th St., #9A, New York, NY (US) 10009

( * ) Notice: Subject to any disclaimer, the term of this patent is extended or adjusted under 35 U.S.C. 154(b) by 0 days.

(21) Appl. No.: 11/229,641

(22) Filed: Sep. 20, 2005

(65) Prior Publication Data
US 2007/0065500 A1    Mar. 22, 2007

(51) Int. Cl.
A61K 36/82    (2006.01)
A61K 36/48    (2006.01)
(52) U.S. Cl. .................................. 424/729; 424/757
(58) Field of Classification Search ........................ None
See application file for complete search history.

(56) References Cited

U.S. PATENT DOCUMENTS 6,664,287 B2 * 12/2003 Avery et al. .................. 514/436
2003/0064937 A1 * 4/2003 Nieuwenhuizen et al. ..... 514/27
2004/0043056 A1    3/2004 Hwang et al.

OTHER PUBLICATIONS http://web.archive.org/web/*/http://www.powersupplements.com/carb-ingredients.html (Web Publication Date: Jul. 15, 2004). Date Accessed: Apr. 26, 2007.*
http://www.vpico.com/articlemanager/printerfriendly.aspx?article=80944 (Posted on: Oct. 15, 2001). Date Accessed: Apr. 26, 2007.*
http://web.archive.org/web/*/http://www.bodybuilding.com/store/hns/phase.html (Web Publication Date: Feb. 20, 2005). Date Accessed: Apr. 26, 2007.*
http://www.vortexhealth.net/phase2.html. Date Accessed: Apr. 26, 2007.*
Birketvedt G. S.; Travis, A.; Langbakk B.; and Florholmen J. R. Nutrition. 2002: 18; 729-733.*
Marshall J. J. and Lauda C. M. J. Biol. Chem. 1975; 250(20): 8030-8037.*
Papagiannopoulos M.; Wollseifen, H. R.; Mellenthin, A.; Haber, B.; and Galensa, R. J. Agric. Food Chem, 2004; 52: 3784-3791.*
Yam, T. S.; Shah, S.; and Hamilton-Miller, J. M. T. FEMS Microbiol. Lett. 1997; 152: 169-174.*
Katiyar S. K.; Afaq, F.; Perez, A.; and Mukhtar, H. Carcinogenesis. 2001; 22(2): 287-294.*
http://web.archive.org/web/*/http://www.bodybuilding.com/store/bioc/carb.html (Web Publication Date: Aug. 3, 2004), Date Accessed: Apr. 26, 2007.*
http://www.henriettesherbal.com/eclectic/kings/pilula.html. Felter, H. W. and Lloyd, J. U. King's American Dispensatory. 1898.*
http://web.archive.org/web/*/http://www.wonderlabs.com/empty-capsules/index.html (Web Publication Date: Apr. 1, 2004). Date Accessed: Apr. 26, 2007.*
http://web.archive.org/web/*/http://www.drugstore.com/qxp79417_333181_sespider/one_a_day/
weight_smart_dietary_supplement_tablets.htm (Web Publication Date: Mar. 8, 2003), Date Accessed: Apr. 26, 2007.*
http://web.archive.org/web/*/http://www.splinfo.com/lifepak_challenge.criteria.htm (Web Publication Date: Aug. 14, 2004), Date Accessed: Apr. 26, 2007.*
Alfier et al., Fiber Intake of Normal Weight, Moderately Obese and Severely Obese Subjects, Obesity Research, vol. 3, No. 6, Nov. 1995.
Alic, M. "Green Tea for Remission Maintenance in Crohn's Disease?", AJG, vol. 94, No. 6, 1999.
Bazzano et al., "Dietary Intake of Folate and Risk of Stroke in US Men and Women—NHANES I Epidemiologic Follow-Up Study", DOI: 10.1161/01.STR,0000014607.90464.88.
Bennett et al., "Benefits of Dietary Fiber—Myth or Medicine?", vol. 99/No. 2/Feb. 1996/Postgraduate Medicine—Dietary Fiber.
Brown, Michael "Green Tea (Camellia Sinensis) Extract and Its Possible Role in the Prevention of Cancer", Alternative Medicine Review, vol. 4, No. 5, 1999.
Brown, L. et al., "Cholesterol-lowering effects of dietary fiber: a meta-analysis", Am J Clin Nutr 1999; 69:30-42.
Bushman, J. "Green Tea and Cancer in Humans: A Review of the Literature", Nutrition and Cancer, 31(3), 151-159.
Dulloo, A. et al., "Efficacy of a green tea extract rich in catechin polyphenols and caffeine in increasing 24-h energy expenditure and fat oxidation in humans", Am J Clin Nur 1999; 70:1040-5.
Foy, C.J. et al., "Plasma chain-breaking antioxidants in Alzheimer's disease, vascular dementia and Parkinson's disease", Q J Med 1999; 92:39-45.
Fujiki, H. et al., "Cancer Inhibition by green tea", Mutation Research 402 (1998) 307-310.
Fujiki, H. et al., "Mechanistic Findings of Green Tea as Cancer Preventive of Humans (44370)", Proc. Soc. Exp. Biol. Med. 220(4): 225-228.
Gao, Y. et al., "Reduced Risk of Esophageal Cancer Associated with Green Tea Consumption", Journal of the National Cancer Institute, vol. 86, No. 11, Jun. 1, 1994.

(Continued)

Primary Examiner—Christopher R. Tate
Assistant Examiner—Melenie McCormick
(74) Attorney, Agent, or Firm—Milbank, Tweed, Hadley & McCloy LLP

(57) ABSTRACT

The present invention is for composition containing extract of Northern White Kidney Bean (*Phaseolus vulgaris*), extract of Red Kidney Bean (*Phaseolus vulgaris*) and extract of Green Tea (*Camellia Sinensis* ). This invention as a supplemental compound, aids in weight reduction both in overweight and obese individuals. This invention helps normal weight subjects in improving their quality of life by maintaining their normal weight. Included is also folic acid, ($B_6$) and $B_{12}$ and the whole supplement is bound by a vegetable matrix. The present invention is directed to methods for inducing weight loss by inhibit the absorption of dietary lipids and starch, increase the metabolic rate and decrease the amino acid homocysteine in the blood, an amino acid known to cause risk of heart disease, by administering a composition of the invention. Due to the content of the green tea extract this invention is also meant to reduce and prevent occurrence of gastrointestinal cancer and cancer of the prostate.

14 Claims, No Drawings

OTHER PUBLICATIONS

Geleijnse, J. et al., "Tea Flavonoids May Protect Against Atherosclerosis", Archn Intern Med. 1999: 159:2170-2174.

Hillman, L. et al., "The effects of the fiber components pectin, cellulose and lignin on serum cholesterol levels 1-3", The American Journal of Clinical Nutrition 42: Apr. 1985, pp. 207-213.

Hirose, M. et al., "Inhibition of mammary gland carcinogenesis by green tea catechins and other naturally occurring antioxidants in female Sprague-Dawley rats pretreated with 7, 12-dimethylbenzlalanthracene", Cancer Letters 83 (1994) 149-156.

Hofield, G. "Beans", Agricultural Research/Sep. 2000.

Krotkiewski, M. "Effect of guar gum on body-weight, hunger ratings and metabolism in obese subjects", British Journal of Nutrition (1984), 52, 97-105.

Levine, A. et al., "Effect of breakfast cereals on short-term food intake 1-3", Am J. Clin Nutr 1989: 50:1303-7.

Liu, S. et al., "Relation between changes in intakes of dietary fiber and grain products and changes in weight and development of obesity among middle-aged women 1-3", Am J Clin Nutr 2003; 278:920-7.

Maxwell, C. et al., "Serum Folate Levels and Subsequent Adverse Cerebrovascular Outcomes in Elderly Persons", Dement Geriatr Cogn Disord 2002; 13:225-234.

McLean, R. et al., "Homocysteine as a Predictive Factor for Hip Fracture in Older Persons", N Engl J Med 350;20 www.nejm.org May 13, 2004.

Mukhtar, H. et al., "Tea Components: Antimutagenic and Anticarcionogenic Effects 1, 2", Preventive Medicine 21, 351-360 (1992).

Nelson, L. et al., "Diet composition related to body fat in a multivariate study of 203 men", Journal of the American Dietetic Association, Aug. 1996, vol. 96, No. 8.

Nourhashemi, F. et al., "Alzheimer disease: protective factos 1-2", Am J Clin Nutr 2000;71(Suppl):643S-9S.

Scheen, S.J. "Management of the metabolic syndrome", Minerva Endocrinol 2004; 29:31-45.

Seshadri, S. et al., "Plasma Homocyteine as a Risk Factor for Dementia and Alzheimer's Disease", N Engl J Med, vol. 346, No. 7, Feb. 14, 2002.

Sen, S. et al., "Risk Factors for Progression of Aortic Atheroma in Stroke and Transient Ischemic Attack Patients", Stroke 33: 930-5, 2002.

Shoskes, D. et al., "Quercetin in Men with Category III Chronic Prostatitis: A Preliminary Prospective, Double-Blind, Placebo-Controlled Trial", Urology 54 (6), 1999.

Slavin, J. "Dietary fiber: Classification, chemical analyses, and food sources", J. Am. Diet. Assoc. 87: 1164.

Forman, J. et al., "Folate Intake and the Risk of Incident Hypertension Among US Women", JAMA, Jan. 19, 2005—Vo. 293, No. 3.

Wolk, A. et al., "Long-term Intake of Dietary Fiber and Decreased Risk of Coronary Heart Disease Among Women", JAMA, Jun. 2, 1999—vol. 281, No. 21.

Yap, S. et al., "Vascular Complications of Severe Hyperphomocysteinemia in Patients with Homocystinuria Due to Cystathionine B-Synthase Deficiency: Effects of Homocysteine-Lowering Therapy", Seminars in Thrombosis and Hemostasis—vol. 26, No. 3, 2000.

Birketvedt et al., "Dietary Supplemental With Bean Extract Improves Lipid Profile in Overweight and Obese Subjects", Nutrition 18:729-733, 2002.

Birketvedt et al., "A Dietary Supplement with Bean Extract Decreases Body Weight, Body Fat, Waist Circumference and Bloof Pressure in Over-Weigh and Obese Subjects", Current Topics in Nutraceutical Research, vol. 3, No. 2, pp. 137-142, 2005.

Birketvedt et al., "Long Term Effect of Fibre Supplement and Reduced Energy Intake on Body Weight and Blood Lipids in Overweight Subjects", ACTA, MEDICA (Hradec Kralove) 2000; 43 (3): 129-132.

International Search Report and Written Opinion for PCT/US2006/035683 dated Feb. 23, 2007.

Xunluo, C. et al., "Bean Flavor Health Tea", Database TCM, SIPO, Abstract, CN1104437, Jul. 5, 1995.

Hamdaoui, M., et al., "Iron bioavailability and weight gains to iron-deficient rats fed a commonly consumed Tunisian meal 'bean seeds ragout' with or without beef and with green or black tea decoction", J. Trace Elem. Med. Biol. vol. 17 (13) 159-164 (2003).

Petlevski, R., et al., "Effect of 'antidiabetis' herbal preparation on serum glucose and fructosamine in NOD mice", Journal of Ethnopharmacology 75 (2001) 181-184.

Udani, Jay, et al., "Blocking Carbohydrate Absorption and Weight Loss: A Clinical Trial Using Phase 2 Brand Proprietary Fractionated White Bean Extract", Alternative Medicine Review, Thorne Research Inc., Sandpoint, US, vol. 9, No. 1, 2004, pp. 63-69.

* cited by examiner

COMPOSITION FOR TREATING OBESITY COMPRISING EXTRACT FROM WHITE KIDNEY BEANS, RED KIDNEY BEANS, AND GREEN TEA LEAVES

FIELD OF INVENTION

This invention relates to the field of treating obesity, associated metabolic and physical aberrations such as altered plasma lipid profile and elevated blood pressure.

BACKGROUND

Obesity is rapidly becoming a major health problem in modern society. It is increasing in prevalence in all developing countries, and in the United States it has reached epidemic proportions. For instance, one in five Americans are obese and one in three are overweight. Of the 67 million overweight and obese Americans, nearly 20 million also have hyperlipidemia. Almost one million Americans die annually from cardiovascular disease and the annual-treatment costs for cardiovascular diseases are an estimated $78.6.

An individual is considered obese when his or her body mass index, or BMI (defined as weight in kilograms divided by the square of height in meters) is greater than 30 kg/m$^2$. Compared to individuals of normal weight (BMI between about 20 and 25kg/m$^2$), overweight (BMI between about 25 and 30 kg/m$^2$) and obese individuals have an increased risk of developing diabetes, cardiovascular disease, hyperlipidemia, arthroses, cancer and other chronic diseases.

Poor nutrition is linked to hyperlipidemia, obesity, hypertension and diabetes, which contribute to the development of cardiovascular disease. Hypercholesterolemia is one of the most important diet-related risk factors for coronary heart disease. More than half of the middle-aged men and women in the United States have serum cholesterol values exceeding 200 mg/dl, values that significantly increase their risk for coronary heart disease.

Because weight-loss and weight-management regimens have frequently been ineffective, effective medical interventions to manage weight gain and slow or prevent progression to obesity are needed. Obesity prevention strategies that begin in early childhood are most effective. Food education program that teach the distinction between healthy food rich in fiber and unhealthy processed food with little fiber content at all are also a necessary component of obesity prevention strategies.

Several studies have indicated that fiber-rich foods and fiber supplements have moderate weight reducing effects, and may also improve the lipid profile in overweight and obese individuals. Alfieri et al. (1995) *Obes. Res.* 3: 54; Birketvedt et al. (2000) *Acta Medica* 43: 129; Birketvedt et al. (2005) *Current Topics in Nutraceutical Research* 1; Birketvedt et al. (2002) *Nutrition* 18: 729. Fiber-rich foods and fiber supplements are also important in controlling or preventing hyperlipidemia. Untreated hyperlipidemia prematurely ages the body's arteries and can lead to stroke, heart attack and kidney failure. Identifying which fiber most effectively controls or prevents hyperlipidemia has been the goal of several studies. Glore et al. (1994) *J. Am. Diet. Assoc.* 425: 94; Liu et al. (2003) *Am. J. Clin. Nutr.* 78: 920; Slavin (1987) *J. Am. Diet. Assoc.* 87: 1164; Hillmann et al. (1985) *Am. J. Clin. Nutr.* 42: 207.

Diets high in fiber content have frequently been used to obtain stable energy intake and avoid metabolic disorders caused by obesity. Scheen (2004) *Minerva Endocrinol.* 29(2): 31-45; Krotkiewski (1984) *Br. J. Nutr.* 52(1): 97. These diets also have many other health benefits, such as preventing constipation, hemorrhoids and diverticular disease as well as protecting against colon cancer. Population studies have shown that societies eating a high fiber diet have few obese individuals, while those eating a high fat, low fiber diet have many morbidly obese individuals. Bennet et al. (1996) *Postgrad. Med.* 99: 153-6, 166-8, and 171.

A study of 203 healthy men showed that men with higher BMI ate more dietary fat and more simple carbohydrates than men with lower BMI. Nelson et al. (1996) *J. Am. Diet. Assoc.* 96: 771. Consequently, the heaviest men ate fewer complex carbohydrates and less fiber in their diets. Several other studies have supported the proposition that weight gain is inversely associated with the intake of high fiber, whole-grain foods, but directly proportional to the intake of refined-grain foods. Burley et al. (1989) *Int. Jou. Obe.* 16: 53; Levine et al. (1989) *Am. J. Clin. Nutr.* 50: 1404. These studies indicate the importance of distinguishing whole-grain products from refined-grain products to aid in weight control, hyperlipidemia and cardiovascular disease.

Dietary is another common method used in weight-loss and weight-management regimens. There are numerous publicly-known diets. Several studies have shown that intensive nutrition intervention with diets rich in dietary fiber can lower serum cholesterol concentration by 20-30%, which may decrease the risk of coronary heart disease. Several studies have also suggested combining dietary fiber with a low fat cholesterol diet, as recommended by the American Heart Association. Brown et al. (1999) *Am. J. Clin. Nutr.* 69(1): 30; Wolk et al. (1998, 1999) *J. Am. Med. Assoc.* 2: 281. Dieting, however, is not always successful, and many people fail to lose weight or improve their blood lipid levels. Glore et al., (1994) *J. Am. Diet. Assoc.* 425: 94.

In spite of all the diets that have been proposed over the years to improve health, many people still face the problem of decreased energy output and increased energy intake. The basic failure in finding the correct balance between energy intake and energy expenditure has resulted in increased obesity and BMI. Replacing processed foods with foods rich in fiber and complex carbohydrates is a preferred solution.

Pharmaceutical approaches to weight control have had mixed results. These products, mostly appetite suppressants, have several serious side effects and health consequences. Consequently, appetite suppressants are not a preferred choice. Other pharmaceutical agents interfere with the body's energy-regulatory mechanisms and may have serious negative effects on the central nervous system through neuroendocrine mechanisms. Another or additional weight-control or weight-reduction approach is to reduce the digestion of starch and the resultant production and absorption of simple sugars. Inhibiting the digestion of starch reduces carbohydrate absorption. The effective inhibition of starch breakdown and the resultant production of simple sugars that alter plasma lipid profiles and promote weight gain, has important implications in the field of weight loss. Phaseolamin, a glycoprotein found mainly in white and red kidney beans, is a known amylase inhibitor the main responsible for the breakdown or digestion of starch. The digestion of starch, which is the main source of carbohydrates in the human diet, begins when food is chewed and mixed with saliva containing α-amylase that randomly hydrolyzes the α(1-4) glycosidic bonds of starch. Because α-amylase cannot cleave the terminal glucosidic bonds and branch points of starch, digestion in the mouth is incomplete. The average chain length, however, is generally reduced from several thousand to less than eight glucose units.

Commercially-available crude bean amylase inhibitors have failed to influence fecal caloric excretion. In addition, many of these commercially available amylase inhibitors cause side effects, such as diarrhea and abdominal discomfort. However, one long term published randomized placebo-controlled study has shown that only minor side effects occurred after intake of a supplement (Wellex) consisting of northern white kidney bean (150 mg) missed with an extract of locust bean gum (25 mg). The same supplement also showed an increased secretion of fat in feces measured in four subjects. Birketvedt et al (2002) *Nutrition* 18: 729.

In a long term study, the use of the white kidney bean extract mixed with extract of locust bean gum has been shown to have lipid controlling effects. Birketvedt et al. (2002) *Nutrition* 18: 729.

SUMMARY OF INVENTION

The present invention provides a composition comprising an extract from white kidney bean, an extract from red kidney bean, and an extract from green tea. Preferably, the white bean extract is water soluble. Preferably, the red bean extract is water soluble. Preferably, the green tea extract is water soluble. In a preferred embodiment, the white kidney bean is *Phaseolus vulgaris*. In another preferred embodiment the red kidney bean is *Phaseolus vulgaris*. In yet another preferred embodiment, the green tea is *Camellia sinensis*.

The present invention also provides a composition comprising an extract from white kidney bean, an extract from green tea and a seed-coat extract from red kidney bean. Preferably, the seed-coat extract from a red kidney bean is water soluble. In a preferred embodiment, the red kidney bean is *Ceratonia siliqua*.

The present invention also provides a composition comprising an extract from white kidney bean, an extract from green tea, an extract from red kidney bean, and further comprising vitamin $B_{12}$, blueberry extract and/or folic acid.

The present invention also provides a composition comprising an extract from white kidney bean, an extract from green tea, a seed-coat extract from red kidney bean, and further comprising vitamin $B_{12}$, blueberry extract, and/or folic acid.

In one embodiment, the compositions of the present invention comprise a white kidney bean extract that is enriched for phaseolamin as compared to a whole-bean extract. In another embodiment, the compositions of the present invention comprise a red kidney bean extract is enriched for flavonoids compared to a whole-bean extract.

The compositions of the present invention may further comprise a pharmaceutically acceptable carrier. In one embodiment the pharmaceutically acceptable carrier is calcium sulfate.

In one embodiment, the compositions of the present invention are formulated as a vegetable capsule. In a preferred embodiment, the vegetable capsule has a disintegration time of not greater than 45 minutes when administered orally.

In one embodiment, the composition of the present invention contains at least 100 milligrams of white kidney bean extract. In one embodiment, the composition of the present invention contains between about 100 and about 1,000 milligrams white kidney bean extract, between about 150 and about 1000 milligrams of white kidney bean extract, between about 200 and about 1000 milligrams of white kidney bean extract, between about 250 and about 1000 milligrams of white kidney bean extract, between about 300milligrams and about 1000 milligrams of white kidney bean extract, between about 350milligrams and about 1000 milligrams of white kidney bean extract, between about 400 and about 1000 milligrams of white kidney bean extract, between about 450 milligrams and about 1000 milligrams of white kidney bean extract, between about 500 milligrams and about 1000 milligrams of white kidney bean extract, between about 550 and about 1000milligrams of white kidney bean extract, between about 600 milligrams and about 1000milligrams of white kidney bean extract, between about 650 milligrams and about 1000milligrams of white kidney bean extract, between about 700 and about 1000 milligrams of white kidney bean extract, between about 750 milligrams and about 1000 milligrams of white kidney bean extract, between about 800 milligrams and about 1000 milligrams of white kidney bean extract, between about 850 and about 1000 milligrams of white kidney bean extract, between about 900 milligrams and about 1000 milligrams of white kidney bean extract, between about 950 milligrams or about 1000 milligrams of white kidney bean extract.

In one embodiment, the composition of the present invention contains about 125 milligrams of white kidney bean extract, about 175 milligrams of white kidney bean extract, about 225 milligrams of white kidney bean extract, about 275 milligrams of white kidney bean extract, about 325 milligrams of white kidney bean extract, about 375milligrams of white kidney bean extract, about 425 milligrams of white kidney bean extract, about 475 milligrams of white kidney bean extract, about 525 milligrams of white kidney bean extract, about 575 milligrams of white kidney bean extract, about 625milligrams of white kidney bean extract, about 675 milligrams of white kidney bean extract, about 725 milligrams of white kidney bean extract, about 775 milligrams of white kidney bean extract, about 825 milligrams of white kidney bean extract, about 875milligrams of white kidney bean extract, about 925 milligrams of white kidney bean extract, or about 975 milligrams of white kidney bean extract. In the most preferred embodiment, the composition of the present invention contains about 200 milligrams of white kidney bean extract.

In yet another embodiment, the compositions of the present invention contain an amount of a white kidney bean extract sufficient to reduce daily carbohydrate absorption—compared to carbohydrate absorption observed in the absence of phaseolamin inhibition of α-amylase—when the composition is administered one, two, three or four times daily.

In one embodiment, the composition of the present invention contains at least 100 milligrams of phaseolamin. In one embodiment, the composition of the present invention contains between about 100 milligrams and about 1 gram phaseolamin, between about 150 milligrams and about 1 gram phaseolamin, between about 200 milligrams and about 1 gram phaseolamin, between about 250 milligrams and about 1 gram phaseolamin, between about 300 milligrams and about 1 gram phaseolamin, between about 350milligrams and about 1 gram phaseolamin, between about 400 milligrams and about 1 gram phaseolamin, between about 450 milligrams and about 1 gram phaseolamin, between about 500 milligrams and about 1 gram phaseolamin, between about 550 milligrams and about 1gram phaseolamin, between about 600 milligrams and about 1 gram phaseolamin, between about 650 milligrams and about 1 gram phaseolamin, between about 700 milligrams and about 1 gram phaseolamin, between about 750 milligrams and about 1 gram phaseolamin, between about 800 milligrams and about 1 gram phaseolamin, between about 850milligrams and about 1 gram phaseolamin, between about 900 milligrams and about 1 gram phaseolamin, or between about 950 milligrams and about 1 gram phaseolamin.

In one embodiment, the composition of the present invention contains about 125 milligrams of phaseolamin, about 175 milligrams of phaseolamin, about 225 milligrams of phaseolamin, about 275 milligrams of phaseolamin, about 325 milligrams of phaseolamin, about 375 milligrams of phaseolamin, about 425 milligrams of phaseolamin, about 475 milligrams of phaseolamin, about 525 milligrams of phaseolamin, about 575 milligrams of phaseolamin, about 625 milligrams of phaseolamin, about 675 milligrams of phaseolamin, about 725 milligrams of phaseolamin, about 775 milligrams of phaseolamin, about 825 milligrams of phaseolamin, about 875 milligrams of phaseolamin, about 925 milligrams of phaseolamin, or about 975 milligrams of phaseolamin. In the most preferred embodiment, the composition of the present invention contains about 200 milligrams of phaseolamin.

In one embodiment, the composition of the present invention contains at least 25 milligrams of red kidney bean extract. In one embodiment, the composition of the present invention contains between about 25 and 250 milligrams of red kidney bean extract, between about 75 and 250 milligrams of red kidney bean extract, between about 125 and 250 milligrams of red kidney bean extract, between about 175 and 250 milligrams of red kidney bean extract, or between about 225 and 250 milligrams of red kidney bean extract.

In one embodiment, the composition of the present invention contains about 100 milligrams of red kidney bean extract, about 150 milligrams of red kidney bean extract, or about 200 milligrams of red kidney bean extract. In the most preferred embodiment, the composition of the present invention contains about 50 milligrams of red kidney bean extract.

In one embodiment, the composition of the present invention contains at least 10 milligrams of green tea extract. In one embodiment, the composition of the present invention contains between about 10 and 500 milligrams green tea extract, between about 25 and 500 milligrams green tea extract, between about 75 and 500 milligrams green tea extract, between about 125 and 500 milligrams green tea extract, between about 175 and 500 milligrams green tea extract, between about 225 and 500 milligrams green tea extract, between about 275 and 500 milligrams green tea extract, between about 325 and 500 milligrams green tea extract, between about 375 and 500 milligrams green tea extract, between about 425 and 500 milligrams green tea extract, or between about 475 and 500 milligrams green tea extract.

In one embodiment, the composition of the present invention contains about 50 milligrams green tea extract, about 150 milligrams green tea extract, about 200 milligrams green tea extract, about 250 milligrams green tea extract, about 300 milligrams green tea extract, about 350 milligrams green tea extract, about 400 milligrams green tea extract, or about 450 milligrams green tea extract. In the most preferred embodiment, the composition of the present invention contains about 100 milligrams green tea extract.

The present invention provides a method for promoting weight loss comprising the step of administering a therapeutically effective amount of a composition of the present invention to a subject in need thereof, wherein the administration of said composition promotes weight loss. In on embodiment, the composition of the present invention is administered orally.

In one embodiment, the compositions of the present invention are administered to an overweight subject with a BMI between about 25 kg/m$^2$ and 30 kg/m$^2$. In another embodiment, the compositions of the present invention are administered to an obese subject with a BMI greater than 30 kg/m$^2$.

The present invention provides a method for reducing elevated blood pressure comprising the step of administering a therapeutically effective amount of the composition of the present invention to a subject in need thereof, wherein the administration of said composition reduces elevated blood pressure. In one embodiment, the composition of the present invention is administered orally. In one embodiment, administration of a composition of the present invention reduces systolic and/or diastolic blood pressure by at least 6%, 7%, 8%, 9%, 10%, 11%, 12%, 13%, 14%, 15%, 16%, 17%, 18%, 19%, 20%, 21%, 22%, 23%, 24%, or 25%. In one embodiment, administration of a composition of the present invention reduces systolic and/or diastolic blood pressure between about 7 and about 25%, about 10 and about 25%, about 12 and about 25%, about 15 and about 25%, about 17 and about 25%, about 17 and about 25%, about 20 and about 25%, or about 22 and about 25%.

In one embodiment, administration of a composition of the present invention reduces systolic and/or diastolic blood pressure about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, or about 25%. In the most preferred embodiment, administration of a composition of the present invention reduces systolic and/or diastolic blood pressure by at least 5%, between about 5 and about 25%, or about 5%.

In another embodiment, administration of a composition of the present invention reduces systolic and/or diastolic blood pressure by at least 5 mmHg. In a more preferred embodiment, administration of a composition of the present invention reduces systolic and/or diastolic blood pressure by about 5, 6, 7, 8, 9, 10, 11, 12, 13, 14, 15, 16, 17, 18, 19, 20, 21, 22, 23, 24 or 25 mmHg.

In yet another embodiment, administration of a composition of the present invention reduces systolic blood pressure to less than 140 mmHg and/or diastolic blood pressure to less than 90 mmHg. In a more preferred embodiment, administration of a composition of the present invention reduces systolic blood pressure to less than 130 mmHg and/or diastolic blood pressure to less than 80 mmHg.

In one embodiment, the present invention provides a method for altering a plasma lipid profile comprising the step of administering a therapeutically effective amount of the composition of the present invention to a subject in need thereof, wherein the administration of said composition alters the plasma lipid profile.

In one embodiment, the subject in need thereof has elevated low-density lipoprotein (LDL). In another embodiment, the subject in need thereof has depressed high-density lipoprotein (HDL). In yet another embodiment, the subject in need thereof has a depressed HDL to LDL ratio.

In a preferred embodiment, the present invention provides a method for altering a plasma lipid profile comprising the step of administering a therapeutically effective amount of the composition of the present invention to a subject in need thereof, wherein the administration of said composition reduces plasma LDL.

In another preferred embodiment, the present invention provides a method for altering a plasma lipid profile comprising the step of administering a therapeutically effective amount of the composition of the present invention to a subject in need thereof, wherein the administration of said composition alters the plasma lipid profile, wherein administration of said composition increases plasma HDL.

In another preferred embodiment, the present invention provides a method for altering a plasma lipid profile comprising the step of administering a therapeutically effective amount of the composition of the present invention to a subject in need thereof, wherein the administration of said composition alters the plasma lipid profile, wherein administration of said increases the ratio of HDL to LDL.

In another embodiment, the present invention provides a method for altering a plasma lipid profile comprising the step of administering a therapeutically effective amount of the composition of the present invention to a subject in need thereof, wherein the administration of said composition alters the plasma lipid profile, wherein administration of said composition reduces total plasma cholesterol.

The present invention provides a method of making the composition of the present invention, comprising the steps of providing a white kidney bean, red kidney bean and green tea extract and combining said extracts. Preferably, the white bean extract is water soluble. Preferably, the red bean extract is water soluble. Preferably, the green tea extract is water soluble. In a preferred embodiment, the white kidney bean is *Phaseolus vulgaris*. In another preferred embodiment the red kidney bean is *Phaseolus vulgaris*. In yet another preferred embodiment, the green tea is *Camellia sinensis*. In one embodiment, the white kidney bean extract that is enriched for phaseolamin as compared to a whole-bean extract. In another embodiment, the compositions of the present invention is enriched for flavonoids compared to a whole-bean extract.

The red kidney bean extracts provided in the production of the compositions of the present invention are preferably seed-coat extracts. Preferably, the seed-coat extract from a red kidney bean is water soluble.

In another embodiment of the present invention, vitamin $B_{12}$, blueberry extract and/or folic acid are further provided and combined with the white kidney bean, red kidney bean and green tea extracts.

In another embodiment of the present invention, vitamin $B_{12}$, blueberry extract and/or folic acid are further provided and combined with the white kidney bean, green tea, and a seed-coat extract from red kidney bean.

In yet another embodiment of the present invention, a pharmaceutically acceptable carrier is further provided and combined with the compositions of the present invention. In one embodiment the pharmaceutically acceptable carrier is calcium sulfate.

In another embodiment, the green tea extract provided in the production of the compositions of the present invention is enriched for catechols compared to a whole tea-leaf extract. In one embodiment, the green tea extract contains between about 2 and 100% catechols by weight, between about 5 and 100% catechols by weight, between about 10 and 100% catechols by weight, between about 20 and 100% catechols by weight, between about 30 and 100% catechols by weight, between about 10 and 100% catechols by weight, between about 50 and 100% catechols by weight, between about 5 and 100% catechols by weight, or between about 20 and 50% catechols by weight. In a more preferred embodiment the green tea extract contains between about 20 and 30% catechols by weight.

In one embodiment the green tea extract contains about 2% catechols by weight, about 5% catechols by weight, about 10% catechols by weight, about 15% catechols by weight, or about 20% catechols by weight, about 30% catechols by weight. In the most preferred embodiment, the green tea extract contains about 25% catechols by weight.

In one embodiment, the green tea extract provided in the production of the compositions of the present invention is enriched for polyphenols. In one embodiment, the green tea extract contains between about 2 and 100% polyphenols, between about 5 and 100% polyphenols, between about 10 and 100% polyphenols, between about 20 and 100% polyphenols, between about 30 and 100% polyphenols, between about 50 and 100% polyphenols, between about 10 and 50% polyphenols, or between about 10 and 25% polyphenols. In a more preferred embodiment, the green tea extract contains between about 10 and 20% polyphenols.

In one embodiment, the green tea extract contains about 2% polyphenols, about 5% polyphenols, about 10% polyphenols, about 15% polyphenols, about 20% polyphenols, about 25% polyphenols, about 30% polyphenols, about 50% polyphenols, or about 75% polyphenols In the most preferred embodiment, the green tea extract contains about 17% polyphenols.

In one embodiment, the green tea extract provided in the production of the compositions of the present invention contains between about 2 and 100% caffeine by weight, between about 5 and 100% caffeine by weight, about 10 and 100% caffeine by weight, between about 20 and 100% caffeine by weight, about 30 and 100% caffeine by weight, between about 40 and 100% caffeine by weight, between about 50 and 100% caffeine by weight, about 60 and 100% caffeine by weight, between about 70 and 100% caffeine by weight, between about 80 and 100% caffeine by weight, about 90 and 100% caffeine by weight, between about 5 and 50% caffeine by weight, between about 5 and 25% caffeine by weight, or between about 20 and 30% caffeine by weight. In the most preferred embodiment, the green tea extract provided in the production of the compositions of the present invention contains between about 5 and 10% caffeine by weight.

DETAILED DESCRIPTION OF INVENTION

Definitions

As used herein, "a therapeutically effective amount" is an amount sufficient to produce a therapeutic response. An effective amount may be determined with dose escalation studies in open-labeled clinical trials or bin studies with blinded trials.

As used herein, the term "pharmaceutically acceptable carrier" means a chemical composition, compound, or solvent with which an active ingredient may be combined and which, following the combination, can be used to administer the active ingredient to a subject.

A "pharmaceutically acceptable carrier", as used herein, includes, but is not limited to, one or more of the following: excipients; surface active agents; dispersing agents; inert diluents; granulating and disintegrating agents; binding agents; lubricating agents; preservatives; physiologically degradable compositions such as gelatin and vegetable paste; aqueous vehicles and solvents; oily vehicles and solvents; suspending agents; dispersing or wetting agents; emulsifying agents, demulcents; buffers; salts; thickening agents; fillers; antioxidants; stabilizing agents; and pharmaceutically acceptable polymeric or hydrophobic materials and other ingredients known in the art and described, for example in Genaro, ed., 1985, *Remington's Pharmaceutical Sciences*, Mack Publishing Co., Easton, Pa., which is incorporated herein by reference.

Energy

The human body expends energy metabolism, muscular work and thermogenesis. This expenditure is compensated for by the energy supplied by the assimilation of foods. If the amount of energy supplied from the dietary foods is identical to the amount of energy a person expends, the individual will maintain a stable weight. If there is an excess supply of energy, the body stores this energy in the forms of fat and gains weight. If there is a deficit in the amount of energy ingested, the body starts to draw the energy it lacks by burning off the fats stored, and the person will lose weight. Often, however, when a body is faced with an energy deficit, the body reacts to save energy and reduce thermogenesis. This is the control mechanisms which accounts for the failure of weight-reducing diets. Specifically, after losing weight for a few weeks, the person's weight stabilizes, and if he or she wishes to lose further weight, he or she will need to reduce the food intake.

Various chemical substances stimulate thermogenesis, such as nicotine, ephedrine, aspirin, caffeine etc. None of these substances have made it possible to produce a medicinal product for treating obesity since the doses required to obtain an increase in thermogenesis entail considerable side effects, which are incompatible with a treatment which is necessarily long-lasting generally extended over several months.

White Kidney Bean Extract

Reducing calorie intake may be achieved by reducing and inhibiting the absorption of carbohydrates. Specifically, reducing the digestion of starch reduced the production of simple sugars that are a major calorie source. Reducing starch metabolism may be achieved by inhibiting α-amylase—an enzyme responsible for the digestion of starch. Phaseolamin, a glycoprotein found mainly in white and red kidney bean, is an effective α-amylase inhibition. Whole, dried non-genetically modified organism (nGMO) Northern White Kidney beans are the preferred source for phaseolamin, but other species and sources of phaseolamin may also be used. The dried beans are milled and suspended placed in aqueous solution.

Phaseolamin may be extracted from the bean by milling and suspending the milled beans in aqueous solution, followed by one or more extraction and purification cycles using methods well-known in the art, such as affinity chromatography. Extracted phaseolamin may be dried by any number of methods, including spray drying and tested for bacterial contamination, mesh (i.e., particle size), moisture content, potency, and organoleptics (i.e. physical characteristics, such as, color, taste, odor, powder, and liquid). Each of these properties may be altered and adjusted by methods well-known in the art.

Red Kidney Bean Extract

Red grapes, oranges, pink grapefruit, strawberries and blueberries all contain colored pigments with nutritious cancer- and heart-disease-fighting compounds called flavonoids. These are the anti-aging antioxidants that may be responsible for the so-called "French paradox", wherein the French tend to have fewer heart attacks and cancers, despite consuming high-fat diets. It is believed that the protective factor could be flavonoids in the skins of red grapes or the wine made from them. Flavonoids are also known to be in many other fruits and vegetables, as well as green and black teas and soy protein.

Red kidney bean has high nutritional value. Red kidney beans have high levels of antioxidants, iron, and other vitamins and minerals. Specifically, both light and dark-red varieties of kidney bean are rich in flavonoids. Hosfield (2000) *Agri. Res. Mag.* Specifically, the kidney bean seed coat, which is 10 percent of the bean, is enriched for flavonoids, antioxidants and fiber. Hosfield and his colleagues found eight flavonoids in the red kidney bean seed coat, six of which were particularly strong antioxidants. They also identified a genetic link between bean color and flavonoids. A link between the presence of one flavonoid and resistance to bean mosaic disease was also identified. This is the first time a specific flavonoid has been associated with a bean color gene.

Using modern molecular genetic technology, pharmaceutical firms could mass-produce these flavonoids, adding beans to the growing list of foods used to make flavonoid supplements. Further, now that Hosfield and colleagues have begun to break the genetic codes of the flavonoids, breeders could increase the amount of flavonoids in beans through traditional breeding or genetic engineering, or a combination thereof. The compositions disclosed herein, may contain flavonoids obtained from extracts of nGMO or beans genetically modified to enrich flavonoid content, or other sources, including purified recombinantly or chemically produced flavonoids.

Green Tea Extract

Green tea has been used for thousands of years in Asia as both a beverage and an herbal medicine. Over the past few years, dozens of studies have been conducted on its antioxidative and chemoprotective effects. Research has shown green tea to be effective against a number of conditions, ranging from lowering cholesterol and capturing free radicals to reducing the risks of certain types of cancers. Hirose (1994) *Cancer Letters* 83:149-156; Gao (1994) *J. Nat'l Cancer Inst.* 86:855-858; Muhtar (1992) *Prev. Med.* 21:351-360; Toda (1989) *Nippon Saikingaku Zasshi* 44:669-672.

Green tea extract has been shown to decrease weight in overweight subjects. Dulloo et al. (1999) *Am. J. Clin. Nutr.* 70: 1040-45. Studies published in the December 1999 issues of the *American Journal of Clinical Nutrition and Urology* show that substances which are abundant in green tea extracts may promote weight loss and treat prostatitis, a painful urinary condition. Dulloo et al. (1999) *Amer. J. Clin. Nutr.* 70:1040-45; Shoskes et al. (1999) *Urology* 54(6): 960-963.

After harvesting, the leaves of may be treated two ways. Subjecting the leaves to a fermentation process, transforming the chemical substances they contain, particularly the catechols, produces black tea. Drying the leaves immediately produces green tea.

In addition to catechols, tea contains caffeine, the diuretic effect of which is well known. The diuretic effect is the reason for the traditional use of green tea as a medicinal plant to promote the elimination of water by the kidneys, either in the case of urinary disorders or as a supplement to weight reducing diets. The presence of caffeine is also the reason for the traditional use of tea in conditions of fatigue (asthenia). Epidemiological studies carried out on certain populations have demonstrated the beneficial effects of the chronic ingestion of tea, and more particularly of green tea.

Studies involving long-term consumption of green tea have shown anti-atherogenic effects. These effects are related to the hypocholesterolemic effects shown in several studies. Geleijnse et al. (1999) *Arch. Intern. Med.* 159: 2170-2174. Additionally, these effects are also related to ability of green tea to prevent the oxidation of LDLs in the circulation. Green tea is also known for its anti-mutagenic and anti-carcinogenic effects. It has been shown to reduce the risk of colorectal, skin cancer and breast cancer in several published studies. Alic (1999) *Am. J. Gastroenterol* 94(6): 1710; Brown (1999) *Alt. Med. Rev.* 4(5): 360-370; Bushman (1998) *Nutr. Cancer* 31(3): 151-159; Fujiki et al. (1998) *Mutation Research* 307-310; Fujiki et al. (1999) *Proc. Soc. Exp. Biol. Med.* 220(4): 225-228; Gao et al. (1994) *J. Nat'l Cancer Inst.* 86(11): 855-8.

As a diuretic, the use of green tea traditionally occurs in the form of infusions, liquid extracts in gel capsules or tables. In those various forms, the green tea, often combined with another diuretic plant, is generally used at a dose corresponding one to three grams of plant per day.

In the present invention, the extract of green tea contains from 20% to 30% by mass of catechols expressed as epigallocatechol gallate (EGCG). The content of catechols, expressed as EGCG is, for example, determined by methods known in the art. The extract of green tea contains from 5% to 10% by mass of caffeine.

The dose of the green tea extract chosen may be based on the average daily calorie intake, based on an analysis of food diaries over a ten-days period. Generally, one milligram green tea extract is used per nine calorie. For example, 300 milligrams of a green tea extract are appropriate for a 2,700 calorie per day diet.

Folic Acid and Vitamin $B_{12}$

Previous studies have shown that women who consume ample amounts of folic acid every day had the lowest risk of hypertension. Sundown (2005) *J. Amer. Med. Assoc.* 3: 320-9. Specifically, it is recommended that every woman should get about 700micrograms daily to boost blood-vessel health and reduce blood pressure. Asparagus spears, artichokes and spinach, fortified pasta, breads and cereals are good folic acid sources.

Typically, obese patients are on a poor diet and have a tendency to eat foods rich in the amino acid homocysteine. Homocysteine is an amino acid in the blood and it has been found that people with moderate to high concentrations of homocysteine and/or homocystinuria, may have increased risk of thromboembolic events, especially stroke. A supplement with folate and Vitamin $B_{12}$ may reduce the levels of homocysteine and thus reduce the risk of stroke. Additionally, Vitamin $B_{12}$ deficiency is extremely common. Hyperhomocysteinemia is caused by deficiencies in vitamins $B_6$, $B_{12}$ and folic acid. Sehardi et al. (2002) *N. Engl. J. Med.* 346(7): 476-483. The adverse vascular and neurotoxic effects of homocysteine are associated with excess free radical generation (oxidative stress). Foy et al. (1999) *Quart. J. Med.* 92: 39-45. In previous studies, higher levels of Vitamin $B_{12}$ have been associated with lower levels of homocysteine. Homocysteine has been linked to stroke. Importantly, folic acid and $B_{12}$ vitamins may lower plans homocysteine. Studies have shown that vitamin $B_{12}$ has a protective effect in vascular events. Specifically, Vitamin $B_{12}$ may play a key role in lowering total plasma homocysteine, thus preventing subsequent vascular events in patients who have had a nondisabling stroke. Patients in this study by Spence received 2.5 mg folate, and 400 mcg of vitamin $B_{12}$. Spence et al. (2005) *American Stroke Association International Stroke Conference New Orleans.*

A recent meta-analysis of data from 500 stroke events in prospective studies, and 1000 stroke events in retrospective trials, identified a statistically significant positive association between homocysteine levels and stroke in all age groups, independent of smoking, cholesterol and blood pressure. Clarke et al. Homocysteine Metabolism, 3rd International Conference 1-5 Jul. 2001. Abstract 109.

Another study identified the association between elevated homocysteine levels and other risk factors for stroke and the risk of aortic atheroma progression. Sen et al. (2002) *Stroke* 33: 930-5. Fifty-seven stroke patients and twenty-one patients with transient ischemic attack underwent multiplanar transesophageal echocardiograms within one month of symptom onset and again after nine months. Aortic atheroma was graded and stratified. Use of anticoagulant, antiplatelet, and hypolipidemic drugs, and clinical and aetiological subtypes of stroke were recorded and compared in patients stratified for the presence or absence of atheroma progression. The only factors that significantly correlated with atheroma progression were homocysteine levels of 14.0 μmol/L or greater, total anterior cerebral infarct, and large-artery atherosclerosis.

It is known that silent brain infarcts and white matter lesions are associated with increased risk of both stroke and dementia. Other recently published data from the Rotterdam Scan study, a population-based study of 1,077 people aged 60-90 years, who had cerebral magnetic resonance imaging, showed that the overall risk of having either silent brain infarcts or severe white matter lesions was strongly associated with elevated homocysteine levels. Vermeer et al. (2002) *Ann. Neurol.,* 51:285-9.

Specifically, twenty percent of the population had one or more silent brain infarcts, 80% had periventricular white matter lesions, and 92% subcortical lesions. Silent brain infarcts were 2.5 times more common in the top quintile of homocysteine concentrations (less than 13.8 μmol/L) compared with the bottom quintile (less than 8.5μmol/L). The risk of silent brain infarct increased by 24% per standard deviation increase of homocysteine. The relationship was continuous and graded, with no obvious threshold below which homocysteine levels were not associated with risk of disease.

A recently published follow-up for 5 years of 369 healthy subjects from the Canadian Study of Health and Aging, showed that the odds ratio of developing vascular dementia/cognitive impairment or fatal stroke was 2.42 for persons with serum folate within the lowest quartile at baseline Maxwell et al. (2002) *Dement. Geriatr. Cogn. Disord.* 13: 225-34.

Estimation of dietary intake of vitamins is less accurate and sensitive than determination of plasma/serum levels. However, an association between calculated folate intake and plasma/serum levels was recently demonstrated. In a follow-up study within the Third National Health and Nutrition Examination Survey (NHANES I) dietary intake of folate was assessed at baseline among 9,764 US men and women aged 25-74 years and free of cardiovascular disease. A 24-hour dietary recall was used. Over an average of 19 years of follow-up, 926 incident stroke events and 3,758 incident cardiovascular events were documented. The occurrence rate for incident stroke for subjects with folate intake within the highest quartile at baseline was calculated to be 0.79 and 0.86 for incident cardiovascular events compared with subjects within the lowest quartile of folate intake. The calculated median-folate intake in the highest quartile was 405 μg/day, and in the lowest 99 μg/day. Bazzano et al. (2002) *Stroke* 33: 1183-9.

Large intervention studies with homocysteine-lowering therapy, designed to show the effect of prevention of stroke occurrence in a general population (or recurrence in patients) are ongoing. An increasing number of intervention studies using surrogate endpoints, such as effects on coagulation factors, and effect on intima plaque formation, in order to assess the effect on coagulation and atherogenesis, have been published. These studies have demonstrated an effect of homocysteine-lowering therapy on both coagulation and the rate of progression of plaque formation. Yap et al., (2000) *Seminars in Thrombosis and Hemostasis,* 26:335-40. Elevated plasma homocysteine (hyperhomocysteinemia) is now recognized as a strong, independent risk factor for stroke and dementia.

Elevated plasma homocysteine, however, is a reversible risk factor. Consumption of foods containing B vitamins and supplementation with folic acid and vitamins $B_6$ and $B_{12}$ are the primary preventive and therapeutic treatments. The intake of antioxidants through diet and supplements protects against oxidant stress and helps maintain the normal function of the vascular system and brain. Sehardi et al., (2002) *N. Engl. J. Med.* 346(7): 476-483; Nourhashemi et al. (2000) *Am. J. Clin. Nutr.* 71(2):643S-649S.

Homocysteine is a reliable marker for cardiovascular health and also provide an important clue about the health of your bones. A study from Harvard and Tufts showed that women with the highest levels of homocysteine had almost twice the risk of hip fracture compared to women with the lowest levels. Among men the association was even more pronounced. Specifically, those men with high homocysteine levels had nearly four times the risk of hip fracture as the men whose levels were low. Elevated homocysteine levels appear to be a strong and independent risk factor for osteoporotic fractures in older men and women. McLean et al. (2004) *New Eng. J. Med.* 350:2042-2049.

Studies have shown that homocysteine levels may be controlled with ample amounts of folic acid. However, folic acid may sometimes mask a vitamin $B_{12}$ deficiency. Thus, adding vitamin $B_6$ may make folate more effective. A benefit of the present invention is that it contains both folate and Vitamin $B_{12}$.

Previous studies have shown that the content of vitamins $B_{12}$ and folic acid in white kidney bean extract may decrease during long term use of the extract. Birketvedt, et al. (2002) *Nutrition* 18:729. The compositions of the present invention, which include folic acid for women and vitamin $B_{12}$ for men and women, show no decrease of either folic acid or vitamin $B_{12}$ within these parameters of this study.

EXAMPLES

The following Examples serve to further illustrate the present invention and are not to be construed as limiting its scope in any way.

Example 1:

Weight Loss

Six obese individuals (3 women and 3 men) with a BMI greater than 30kg/m² and with untreated hypertension and high blood lipids, volunteered to participate in a study to examine the efficacy of a green tea extract and phaseolamin—containing supplement in weight reduction. The supplement comprises 200 mg, white kidney bean extract 50 mg, red kidney bean extract, and 100 mg green tea extract, given twice daily, as a capsule half an hour before lunch and dinner. This composition is referred to as the Test Composition throughout the following examples. The individuals were obese and had high plasma-lipid levels, but were otherwise healthy individuals between 43 to 65 years of age, with no known disease and taking no medication. Patients on a weight loss regimen, restricted diet, smokers, patients included in other studies and patients taking diet supplements or vitamins were excluded. Lipids and nutritional blood parameters were measured at baseline and at the end of the study. Excretion of fat in feces was measured at the end of study and after a wash out period of one week. The study lasted for 8 weeks and the results appear in Table 1.

TABLE 1

Weight Loss Following 8-Week Administration of Test Composition

| Patient | Weight at start in kilogram | Weight in kilogram after 8 weeks | Weight in kilogram lost |
|---|---|---|---|
| Patient 1 (P1) | 104.7 | 98.1 | 6.6 |
| Patient 2 (P2) | 108.3 | 101.4 | 6.9 |
| Patient 3 (P3) | 98.4 | 90.2 | 8.2 |
| Patient 4 (P4) | 124.2 | 118.1 | 6.1 |
| Patient 5 (P5) | 143.7 | 136.7 | 7.0 |
| Patient 6 (P6) | 181.4 | 174.3 | 7.1 |

Patients 1, 2 and 3 are female; Patients 4, 5 and 6 are male. The subjects were asked to maintain their own diet and not change their food intake or exercise level. Food intake did change most likely due to the effect of the extract of the green tea. According to weekly diet analyses of food diaries, the following changes took place in each individual. See Table 2.

TABLE 2

Caloric Intake Following 8-Week Administration of Test Composition

| Patient | Week 1 | Week 2 | Week 3 | Week 4 | Week 5 | Week 6 | Week 7 | Week 8 |
|---|---|---|---|---|---|---|---|---|
| P1 | 2300 | 2240 | 2100 | 1980 | 1760 | 1720 | 1730 | 17201 |
| P2 | 2890 | 2740 | 2710 | 2680 | 2450 | 2340 | 2280 | 2260 |
| P3 | 3200 | 3200 | 3100 | 2940 | 2780 | 2430 | 2400 | 2380 |
| P4 | 2430 | 2200 | 1980 | 1870 | 1780 | 1640 | 1720 | 1680 |
| P5 | 1420 | 1400 | 1460 | 1620 | 1520 | 1320 | 1300 | 1320 |
| P6 | 1900 | 1870 | 1920 | 1860 | 1700 | 1430 | 1540 | 1400 |

The observed changes in caloric intake cannot alone account for the extra weight loss. In a Visual Analogue Scale Hunger Rating Questionnaire, given to the six individuals one week before starting the study, the individuals confirmed they were always hungry at meals. The individuals confirmed that they felt less hungry at meals after administration of the Test Composition. The participants also confirmed that they stopped eating once satisfied and ingested fewer calories when taking the Test Composition. Compared to another study with a white kidney bean extract mixed with locust bean gum (Wellex). (Birketvedt et al. (2002) *Nutrition* 18: 729) The participants (P1-P6) felt more satiated faster and therefore ate less. The participants (P1-P6) also lost more weight over a shorter amount of time. In the referenced study with Wellex, the participants lost an average 3.2 kg after 8 weeks compared to an average 5.8 kg for participants P1-P6. (See, Table 1) The weight loss observed for P1-P2 and depicted in Table 1 exceeds the weight loss observed in individuals consuming Wellex. Birketvedt et al. (2002) *Nutrition* 18: 729.

Example 2:

Improved Lipid Profile

The effects of various supplements on plasma lipid profile were studied in a group of individuals using the composition of a supplement containing a white kidney bean extract mixed with locust bean gum (Wellex). Birketvedt et al. (2002) *Nutrition* 18: 729. The effects of the Test Composition, Wellex, and placebo (containing no active ingredients (i.e., no white kidney bean extract, red kidney bean extract or green tea extract) on lipid profile are presented in Table 3.

TABLE 3

Effect of Various Compositions On Plasma Lipid Profile

| | Total Cholesterol (mmol/l) | Triglycerides (mmol/l) | LDL (mmol/l) | HDL (mmol/l) | LDL/HDL (ratio) |
|---|---|---|---|---|---|
| Test Composition | | | | | |
| Start | 6.9 | 1.9 | 4.7 | 1.1 | 3.7 |
| 2 Months | 6.1 | 1.8 | 4.3 | 1.2 | 3.8 |
| Wellex | | | | | |
| Start | 6.6 | 1.8 | 4.4 | 1.3 | 3.6 |
| 3 Months | 6.2 | 1.8 | 4.4 | 1.2 | 3.8 |
| Placebo | | | | | |
| Start | 6.2 | 2.4 | 4.1 | 1. | 3.7 |
| 3 Months | 6.3 | 2.5 | 4.1 | 1.2 | 3.9 |

Example 3:

Body Composition

In the six individuals receiving the Test Composition, each participant's body composition and waist circumference was measured. Body compositions was determined using infrared spectroscopy (NIR, Futrex 5000, Gaithersburg). Waistline measurements are performed at the upper spina iliaca anterior superior underneath the umbilicus. The Test Composition was well tolerated and the participants reported no side effects. The results are shown in Table 4.

The NIR method is based on the principle that the degree of near infrared scattering is related to the composition of the substance through which the near infrared light passes. As such, the NIR method is considered a direct measure of body fat. The Futrex 5000 apparatus consists of a monochromatic wave emitter and a fiber optic probe, which both conducts radiation from the emitter to a site selected on the body (biceps) and detects interactive radiation. The difference between the amount of light absorbed at two wavelengths (940 and 950 nm) is used to calculate the percentage body fat in the tested (representative) locations. The wavelengths must be chosen in a region of the spectrum sensitive to differences in fat levels. Measurements at the midpoint of the biceps show good correlation to underwater weighing. No correction for physical activity was made in this study.

TABLE 4

Indicia of Weight Loss in Subjects Receiving the Test Composition

| | BMI (Kg/m$^2$) | Body Fat (%) | Waist (Cm) |
|---|---|---|---|
| Start | 36.0 | 37.3 | 109.2 |
| 8 Weeks | 32.1 | 31.4 | 103.4 |

The body composition and waist circumference of individuals receiving Wellex (a composition containing white kidney bean extract and locust bean gum extract) are shown in Table 5. Birketvedt et al. (2005) *Current Topics in Neutraceutical Research* 3: 137-142. The composition of the present invention showed a greater weight loss and fat loss as well as decrease in waist circumference than the study with Wellex.

TABLE 5

Indicia of Weight Loss in Subjects Receiving Wellex

| | BMI (Kg/m$^2$) | Body Fat (%) | Waist (Cm) |
|---|---|---|---|
| Wellex | | | |
| Start | 33.9 ± 3.4 | 33.0 ± 5.2 | 108.6 ± 12.2 |
| 3 Months | 32.9 ± 3.3* | 30.2 ± 5.1* | 104.8 ± 12.1* |
| Placebo | | | |
| Start | 35.0 ± 5.4 | 32.2 ± 6.1 | 112.8 ± 13.5 |
| 3 Months | 35.0 ± 5.3 | 31.9 ± 5.8 | 111.4 ± 13.8 |

Example 4:

Blood Pressure

The effect of the Test Composition on the blood pressure of 3 hypertensive men and 3 hypertensive women were measured in an 8 week study. The results are presented in Table 6. The diastolic and systolic blood pressure decreased to a greater degree after 8-week administration of the Test Composition, as compared to studies with Wellex (data not shown). Birketvedt et al. (2005) *Current Topics in Neutraceutical Research* 3: 137-142. See Table 6.

TABLE 6

Effects of Systolic and Diastolic Blood Pressure in Subjects Using the Test Composition

| Test Composition | Systolic BT (mmHg) | Diastolic BT (mmHg) |
|---|---|---|
| Start | 148.6 | 95.5 |
| 2 Months | 137.0 | 85.6 |

I claim:

1. A composition comprising
an extract from white kidney beans;
an extract from red kidney beans; and
an extract from green tea,
wherein the weight ratio of white kidney bean extract to red kidney bean extract to green tea extract is about 200:50:100.

2. A composition comprising
about 175, about 200, about 225, about 275, or about 325 milligrams of an extract from white kidney beans;
an extract from red kidney beans; and
an extract from green tea, wherein the weight ratio of white kidney bean extract to red kidney bean extract to green tea extract is about 200:50:100.

3. A composition comprising
an extract from white kidney beans;
between about 25 and 250 milligrams of an extract from red kidney beans; and
an extract from green tea, wherein the weight ratio of white kidney bean extract to red kidney bean extract to green tea extract is about 200:50:100.

4. A composition comprising
an extract from white kidney beans;
an extract from red kidney beans; and
about 50, about 100, about 150, about 200, or about 250 milligrams of an extract from green tea, wherein the weight ratio of white kidney bean extract to red kidney bean extract to green tea extract is about 200:50:100.

5. The composition of claim 2, wherein the composition contains between about 25 and 250 milligrams of an extract from red kidney beans.

6. The composition of claim 2, wherein the composition contains about 50, about 100, about 150, about 200, or about 250 milligrams of an extract from green tea.

7. The composition of claim 3, wherein the composition contains about 50, about 100, about 150, about 200, or about 250 milligrams of an extract from green tea.

8. The composition of claim 2, wherein the composition contains between about 25 and 250 milligrams of an extract from red kidney beans and about 50, about 100, about 150, about 200, or about 250 milligrams of an extract from green tea.

9. The composition of claim 8, wherein the composition contains about 200 milligrams of white kidney bean extract, about 50 milligrams of red kidney bean extract, and about 100 milligrams great tea extract.

10. A method for promoting weight loss comprising the step of administering a therapeutically effective amount of the composition of claim 8 to a subject in need thereof, wherein the administration of said composition promotes weight loss.

11. The method of claim 10, wherein the composition is administered orally.

12. The method of claim 10, wherein said subject is overweight with a BMI between about 25 kg/m2 and 30 kg/m2.

13. The method of claim 10, wherein said subject is obese with a BMI greater than 30 kg/m2.

14. A method of making a composition comprising combining about 175, about 200, about 225, about 275, or about 325 milligrams of an extract from white kidney beans, between about 25 and 250 milligrams of an extract from red kidney beans, and about 50, about 100, about 150, about 200, or about 250 milligrams of an extract from green tea, wherein the weight ratio of white kidney bean extract to red kidney bean extract to green tea extract is about 200:50:100.

* * * * *